(12) United States Patent
Rizkalla et al.

(10) Patent No.: US 8,487,123 B2
(45) Date of Patent: Jul. 16, 2013

(54) PROCESS FOR INITIATING A HIGHLY SELECTIVE ETHYLENE OXIDE CATALYST

(75) Inventors: Nabil Rizkalla, Rivervale, NJ (US); Norma B. Castagnola, East Windsor, NJ (US); Girish Desai, East Brunswick, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 271 days.

(21) Appl. No.: 12/977,549

(22) Filed: Dec. 23, 2010

(65) Prior Publication Data

US 2011/0152549 A1 Jun. 23, 2011

Related U.S. Application Data

(60) Provisional application No. 61/289,719, filed on Dec. 23, 2009.

(51) Int. Cl.
*C07D 301/03* (2006.01)
(52) U.S. Cl.
USPC .......................... 549/536; 549/537
(58) Field of Classification Search
USPC ................................ 549/536, 537
See application file for complete search history.

(56) References Cited

U.S. PATENT DOCUMENTS

| | | | |
|---|---|---|---|
| 2,279,469 A | 4/1942 | Law et al. | |
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,874,879 A | 10/1989 | Lauritzen et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,155,242 A | 10/1992 | Shankar et al. | |
| 5,187,140 A | 2/1993 | Thorsteinson et al. | |
| 5,407,888 A | 4/1995 | Herzog et al. | |
| 7,102,022 B2 | 9/2006 | Evans et al. | |
| 7,553,980 B2 | 6/2009 | Rizkalla et al. | |
| 2004/0049061 A1 | 3/2004 | Lockemeyer et al. | |
| 2004/0110974 A1 | 6/2004 | Lilga et al. | |
| 2007/0032670 A1 | 2/2007 | Zhang et al. | |
| 2007/0037991 A1 | 2/2007 | Rizkalla | |

FOREIGN PATENT DOCUMENTS

| | | |
|---|---|---|
| EP | 0352850 B1 | 1/1994 |
| GB | 1055147 | 1/1967 |
| WO | WO2004002971 A1 | 1/2004 |

OTHER PUBLICATIONS

International Search Report dated Sep. 14, 2011.

*Primary Examiner* — Taylor Victor Oh
(74) *Attorney, Agent, or Firm* — Scully, Scott, Murphy & Presser, P.C.

(57) ABSTRACT

A start-up process for epoxidation of ethylene is provided. The process includes initiating an epoxidation reaction by reacting a feed gas composition in the presence of an epoxidation catalyst at a first temperature of about 180° C. to about 210° C. The first temperature is increased to a second temperature of about 230° C. to about 290° C., over a time period of about 6 hours to about 50 hours, while simultaneously adding a sufficient concentration of moderator so that the amount of moderator adsorbed on the catalyst after achieving the second temperature is from about 10 to about 50 g/m³ of catalyst. The second temperature is maintained for about 50 hours to about 350 hours, while regulating the feed gas composition to contain about 0.5% to about 25% $CO_2$. The second temperature is decreased to a third temperature, while simultaneously increasing moderator concentration to a level greater than the sufficient concentration.

11 Claims, No Drawings

PROCESS FOR INITIATING A HIGHLY SELECTIVE ETHYLENE OXIDE CATALYST

RELATED APPLICATIONS

This application claims benefit of U.S. Provisional Patent Application Ser. No. 61/289,719, filed Dec. 23, 2009, the entire content of which is incorporated herein by reference.

BACKGROUND OF THE INVENTION

The start-up of a highly selective silver-based catalyst for ethylene oxidation requires a special procedure. The catalyst, especially when it comprises Re as a promoter, requires an initiation period before it is able to give the expected higher performance. In the prior art, Lauritzen, U.S. Pat. No. 4,874,879 and P. Shankar, U.S. Pat. No. 5,155,242, disclosed the prechloriding of fresh Re-containing catalyst before adding oxygen to the feed. In these disclosures, the catalyst was, initially, pre-chlorided with a feed containing ethylene, methane, and ethyl chloride. This was followed by adding oxygen to the feed and the reaction temperature was kept below 273° C. Eventually several adjustments to the reaction conditions were made in order to get the optimum performance. This pre-chloriding step, was claimed to enhance the activity of the rhenium-containing catalysts, and allow start-up at low temperatures.

A further start-up process is disclosed in J. Lockemeyer, U.S. Patent Application Publication No. 2004/0049061. Particularly, the J. Lockemeyer publication claimed a method for improving the selectivity of a supported highly selective epoxidation catalyst, comprising silver in a quantity of at most 0.17 g per $m^2$ surface area of the support, via contacting the catalyst, with a feed comprising oxygen at a catalyst temperature above 250° C. for a duration of up to 150 hours. There was no mention in this disclosure of a moderator soaking step.

Evans, U.S. Pat. No. 7,102,022, claimed a method for the start-up of a process for the epoxidation of an olefin, comprising a silver-based highly selective epoxidation catalyst, via contacting the catalyst bed with feed comprising oxygen. In this treatment, the temperature of the catalyst bed was above 260° C. for a period of at most 150 hours. In addition to oxygen, one or more components selected from the olefin, carbon dioxide, the inert gases and reaction modifiers, such as organic halides can be present in the feed. However, it was stated that the presence of these additional components in the feed is not considered to be essential to the invention. However, when the feed comprised the addition of an organic halide, its concentration was in the range of from 1 to 30 ppm calculated on the basis of the halogen content, relative to the total feed. There was no mention in this disclosure of a moderator soaking step.

The aforementioned publications disclose start-up procedures that may be effective under some circumstances for certain catalysts. However, because of the importance for operating highly selective catalysts under optimum performance conditions, there is a continued need to develop new and improved methods for the start-up of these catalysts.

SUMMARY OF THE INVENTION

The present invention relates to a method for the start-up of a process for the epoxidation of ethylene comprising: initiating an epoxidation reaction by reacting a feed gas composition containing ethylene, and oxygen, in the presence of an epoxidation catalyst at a first temperature of about 180° C. to about 210° C.; increasing the first temperature to a second temperature of about 230° C. to about 290° C., over a time period of about 6 hours to about 50 hours, while simultaneously adding a sufficient concentration of moderator so that the amount of chloride moderator adsorbed on the catalyst after achieving the second temperature is from about 10 to about 50 $g/m^3$ of catalyst; maintaining the second temperature for a time period of about 50 hours, to about 350 hours while regulating the feed gas composition to contain about 0.5% to about 25% $CO_2$; and decreasing the second temperature to a third temperature, while simultaneously increasing moderator concentration to a level greater than the sufficient concentration.

DETAILED DESCRIPTION OF THE INVENTION

The prior art has disclosed that the start-up of a highly selective silver-based catalyst for ethylene oxidation requires a special procedure, being conducted at high temperatures for extended periods. The presence of the moderator in the feed was reported not to be essential to the reported conditioning.

The applicants of the present application have discovered that starting the dosing procedure before ramping up the temperature will lead to a state of oversaturation. On the other hand, dosing the catalyst after the heating up period, to the conditioning temperature, will lead to an uncontrolled reaction in the early phase of the conditioning phase. This invention provides a method to avoid the problems associated with starting the dosing procedure too early or too late. The applicants of the present application have discovered that the "conditioning" of the highly selective silver-based catalyst, especially if it comprises Re as a promoter, is more efficient if the catalyst is dosed with the reaction moderator, in two discrete steps. According to this invention, dosing the catalyst by soaking with halogenated hydrocarbon moderator compounds, should start during the heating up of the catalyst to the second conditioning temperature.

It has also been discovered that with the instant inventive process, the period of time that is needed to saturate the catalyst bed with the assigned Cl-level is considerably shorter than if it were done either before the start of the heat up period or after the heating temperature is achieved.

The second dosing procedure is applied after the conditioning period is concluded. The moderator added after this second step is normally a fraction of the amount that was used in the first dosing step. This second dosing procedure should be applied during, or after, ramping down to the third temperature.

Within the instant embodiment, the moderator typically includes, but is not limited to, organic chlorides such as, but not limited, to chloromethanes, chloroethanes, chloropropanes and other chloroalkanes, as well as chloroalkenes such as vinyl chlorides, and chloropropenes. Other organic chlorides, as well as other organic halides, are not excluded. In one embodiment, the moderator can be selected from a $C_1$-$C_8$ halohydrocarbon. In another embodiment, the moderator can be selected methyl chloride, ethyl chloride, ethylene dichloride and vinyl chloride. In particular, the moderator material is intended to include the effective sum of all the organic chloride (or alternatively organic halide) moieties that are in a feed gas mixture. The quantity of the organic chloride moieties that is in the feed gas mixture is generally in the range of 0.5 to 5 parts per million, by volume.

Prior to performing the inventive start-up procedure, the catalyst may be swept by passing an inert gas such as nitrogen, over the catalyst bed. The inventive start-up procedure begins by first heating up a reactor, including a high selectivity catalyst, over which a gas, for example nitrogen, is flowing, to a first temperature using an available external heat source, for example steam, while staying within the reactor design limitations and maintaining the gas flow to the reactor that is within 25 to 100% of the design rates.

With the aid of the external heat source, the temperature of the reactor is increased to a first temperature that is typically from about 180° C. to about 210° C. Usually the temperature is held for a time period from about 0.15 hour or more. In one embodiment the holding is conducted for a time period from about 0.5 hour to about 48 hours.

Once the reactor has achieved the first temperature, ethylene, and then oxygen are introduced to the reactor feed gas. During this introduction process, the olefin concentration within the reactor builds up to a value that is typically within a range from about 2 to about 15%. The reaction conditions for the early phase of the start-up of the catalyst will show a low selectivity. This is expected since the surface of the fresh catalyst does not contain the well known combustion-inhibiting chloride components. At this low selectivity phase, the feed will contain the minimum level of ethylene and oxygen. It will contain primarily an inert gas, one or a combination of nitrogen, methane and carbon dioxide.

The moderator may be allowed to be added to the feed at the first temperature for the shortest time and the smallest quantity possible. It is, however, preferred to not allow the catalyst to be exposed to the moderator before stating the temperature increase toward the second temperature. Oxygen is typically brought to a concentration that is within a range from about 0.5 to about 3% at the reactor inlet.

During the aforementioned introduction step, the olefin and oxygen concentrations are adjusted to generate enough heat of reaction that will gradually allow raising the reactor temperature to a second temperature, over a time period of about 6 hours to about 50 hours, which is greater than the first temperature. Typically, the second temperature is within a range from about 230° C. to about 290° C. This second temperature is maintained within the reactor for a time period from about 50 to about 350 hours.

The levels of ethylene and oxygen in the feed are assigned to give a self sustaining reaction that is capable of generating the required heat to bring the first temperature to the second temperature. For instance, the ethylene concentration in the feed is in the range of about 1% to about 7%, and preferably in the about 2 to about 5% range. The concentration of oxygen in this heat up phase should be about 0.2% to about 2%, preferably about 0.5% to about 1%. Initially, all the oxygen in the feed is consumed and the reactor effluent will virtually have no oxygen and the selectivity will be in the 40-50% range. These results, however, will last only for the limited heat up period of about 6 hours to 15 hours during which the first temperature is raised to the second temperature.

The concentration of the organic chloride species in the gas feed, during the temperature increase is about 0.2 to about 2 ppm and its precise value is calculated to load the catalyst bed with the assigned amount at the end or after the end of the temperature ramp up to the second temperature. By the time the second temperature is achieved as a result of the temperature increase, the amount of the moderator, e.g., organic chloride, that will be adsorbed "soaked" on the catalyst at this stage is in the range of from 10 to 50 grams per m$^3$ of catalyst. Preferably the amount of the moderator that will be adsorbed on the catalyst at this stage is about 15 to about 40 grams per m$^3$ of catalyst. The moderator is adsorbed by the catalyst until the catalyst reaches a steady state at which point the catalyst will be less active and more selective, hence the presence of both moderator and oxygen in the effluent. (At the end of, or after the end of, the temperature ramp up period, the catalyst will have acquired the saturation level of the Cl species and is ready to produce the epoxidation product, even through the conditioning period.)

The moderator level will be adjusted, reduced to maintain the same level of catalyst saturation and maintain the catalytic performance. During the rest of the conditioning period, the selectivity will improve and the catalyst will be available for EO production at a selectivity in the 80-90% range, depending on the catalyst's composition and reaction parameters. The feed gas composition will be regulated to contain about 0.5% to about 25% $CO_2$ in order to control the catalyst activity within a narrow band around the second temperature. Simultaneous with all the aforementioned adjustments to the feed compositions and work rate, the second temperature is maintained for a period of 50 hours to about 350 hours.

In a further step of the inventive process, the second temperature is lowered to the third (production level) temperature, while simultaneously introducing a higher level of the moderator compound which is on the order of about 0.5 ppm to about 5 ppm, to in effect start a second soaking stage. The feed rate of the moderator is adjusted in order to have the catalyst saturated with the moderator, e.g., organic chloride, at a higher level than its level after the first soak procedure. Thus, the amount of moderator adsorbed on the catalyst after achieving the third temperature is higher than the amount of moderator adsorbed on the catalyst after achieving the second temperature. The total soaked moderator is about 20 g/m$^3$ to about 80 g/m$^3$ of catalyst. This is followed by adjusting the components of the gas feed to the full production's design level.

By the end of this step, the design conditions are as follows:

| | | |
|---|---|---|
| Feed Composition | 8-30% | ethylene |
| | 4-8% | oxygen |
| | 1-25% | Carbon dioxide |
| | 0.2-3.5 ppm | moderator |
| | balance | Inert gas |
| Ethylene oxide in effluent | 1-3% | |
| Selectivity | 80%-92% | |
| GHSV | 3000-8000 | |
| Reaction pressure | 200-400 psig | |
| Reaction temperature | 230-250° C. | |

The preferred design conditions are:

| | | |
|---|---|---|
| Feed Composition | 12-25% | ethylene |
| | 4-7% | oxygen |
| | 1-20% | Carbon dioxide |
| | 0.5-1.0 ppm | moderator |
| | balance | Inert gas |
| Ethylene oxide in effluent | 1.8-2.5% | |
| Selectivity | 85-87% | |
| GHSV | 3500-5000 | |
| Reaction pressure | 250-350 psig | |
| Reaction temperature | 240-250° C. | |

These are essentially production conditions.

A description of the high selectivity catalyst that can be employed in the present invention is now provided. The high selectivity catalyst employed in the present invention is any silver-based supported catalyst which achieves a selectivity that is greater than 83%. The support employed in this invention may be selected from a large number of solid, refractory supports that may be porous. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. A preferred support is comprised of alpha-alumina having a very high purity; i.e., at least 95 wt. % pure, or more preferably, at least 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

The support may be made utilizing conventional techniques well known to those skilled in the art. Alternatively, the support may be purchased from a catalyst support provider.

The support is preferably porous and has a B.E.T. surface area of at most 20 $m^2/g$, preferably from 0.1 to 10 $m^2/g$, and more preferably from 0.5 to 5 $m^2/g$. As used herein, the B.E.T. surface area is deemed to have been measured by the method as described in Brunauer, Emmet and Teller in J. Am. Chem. Soc. 60 (1938) 309-316. The support may have a monomodal pore size distribution or a multi-modal pore size distribution.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range from about 3 mm to about 12 mm, and preferably in the range from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts contain up to about 45% by weight of silver, expressed as metal, based on the total weight of the catalyst including the support. The silver is deposited upon the surface and throughout the pores of a porous refractory support. Silver contents, expressed as metal, from about 1% to about 40% based on the total weight of the catalyst are preferred, while silver contents from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver nitrate, silver oxide, or a silver carboxylate, e.g., silver oxalate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 10 parts per million to about 1000 parts per million, preferably from about 20 parts per million to about 500 parts per million, and more preferably from about 30 parts per million to about 350 parts per million of total catalyst expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include a diamino alkane having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially non-polar. In general, the solvent should have sufficient solvating power to solubilize the solution components. At the same time, it is preferred that the solvent be chosen to avoid having an undue influence on, or interaction with, the solvated promoters.

The concentration of silver in the impregnating solution is typically in the range from about 1.0% by weight up to the maximum solubility afforded by the particular solvent/solubilizing agent combination employed. It is generally very suitable to employ solutions containing from about 5% to about 45% by weight of silver, with concentrations of from about 10 to about 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, rhenium component, alkali metal component, and the optional other promoters, the impregnated support is calcined for a time sufficient to convert the silver containing compound to silver and to remove the volatile components from the impregnated support to result in a catalyst precursor. The calcination may be accomplished by heating the impregnated support, preferably at a gradual rate, to a temperature in the range from about 200° C. to about 600° C., preferably from about 200° C. to about 500° C., and more preferably from about 200° C. to about 450° C., at a pressure in the range from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver compound is converted to silver. Continuous or step-wise heating may be used for this purpose.

During calcination, the impregnated support may be exposed to a gas atmosphere comprising an inert gas or a mixture of an inert gas with from about 10 ppm to about 21% by volume of oxygen.

After calcining the high selectivity catalyst, the calcined catalyst is loaded into reactor tubes of an epoxidation reactor, typically a fixed bed, tubular reactor, utilizing conventional loading methods well known to those skilled in the art. After loading, the catalyst bed may be swept by passing an inert gas such as nitrogen over the catalyst bed.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

We claim:

1. A method for the start-up of a process for the epoxidation of ethylene comprising:
   initiating an epoxidation reaction by reacting a feed gas composition containing ethylene, and oxygen, in the presence of an epoxidation catalyst at a first temperature of about 180° C. to about 210° C.;
   increasing the first temperature to a second temperature of about 230° C. to about 290° C., over a time period of about 6 hours to about 50 hours, while simultaneously adding a sufficient concentration of moderator so that the amount of moderator adsorbed on the catalyst after achieving the second temperature is from about 10 to about 50 g/m$^3$ of catalyst;
   maintaining the second temperature for a time period of about 50 hours to about 350 hours, while regulating the feed gas composition to contain about 0.5% to about 25% $CO_2$; and
   decreasing the second temperature to a third temperature, while simultaneously increasing moderator concentration to a level greater than the sufficient concentration.

2. The method according to claim 1, wherein during the increasing the first temperature the sufficient concentration of moderator is about 0.2 ppm to about 1 ppm.

3. The method according to claim 1, wherein the moderator is an organic halide.

4. The method according to claim 1, wherein the moderator is selected from the group consisting $C_1$ to $C_8$ halohydrocarbons.

5. The method according to claim 1, wherein the moderator is selected from the group consisting of methyl chloride, ethyl chloride, ethylene dichloride and vinyl chloride.

6. The method according to claim 1, wherein during the initiating step the feed gas composition contains about 2% to about 15% ethylene, and about 0.5% to 3% oxygen.

7. The method according to claim 1, wherein during the regulating step the feed gas contains about 8% to about 30% of ethylene and about 4% to about 8% of oxygen.

8. The method according to claim 1, wherein the third temperature is from about 230° C. to about 250° C.

9. The method according to claim 1, wherein the selectivity at the third temperature is from about 80% to about 92%.

10. The method according to claim 1, wherein during the increasing step, the amount of chloride moderator adsorbed on the catalyst is from about 10 to about 40 $g/m^3$ of catalyst.

11. The method according to claim 1, wherein the catalyst after the initiation step has a total chloride content absorbed thereon of from about 20 $g/m^3$ to about 80 $g/m^3$ of catalyst.

* * * * *